(12) United States Patent
Peine (10) Patent No.: US 11,918,299 B2
(45) Date of Patent: Mar. 5, 2024

(54) SYSTEMS AND METHODS FOR DETECTION OF OBJECTS WITHIN A FIELD OF VIEW OF AN IMAGE CAPTURE DEVICE (71) Applicant: Covidien LP, Mansfield, MA (US)

(72) Inventor: William Peine, Ashland, MA (US)

(73) Assignee: COVIDIEN LP, Mansfield, MA (US)

(*) Notice: Subject to any disclaimer, the term of this patent is extended or adjusted under 35 U.S.C. 154(b) by 1006 days.

(21) Appl. No.: 16/615,563

(22) PCT Filed: May 7, 2018

(86) PCT No.: PCT/US2018/031327
§ 371 (c)(1),
(2) Date: Nov. 21, 2019

(87) PCT Pub. No.: WO2018/217433
PCT Pub. Date: Nov. 29, 2018

(65) Prior Publication Data
US 2020/0170718 A1 Jun. 4, 2020

Related U.S. Application Data (60) Provisional application No. 62/511,022, filed on May 25, 2017.

(51) Int. Cl.
*A61B 34/20* (2016.01)
*A61B 34/35* (2016.01)
(Continued)

(52) U.S. Cl.
CPC .............. *A61B 34/20* (2016.02); *A61B 34/35* (2016.02); *A61B 90/37* (2016.02); *G16H 20/40* (2018.01);
(Continued)

(58) Field of Classification Search
CPC ......... A61B 34/20; A61B 34/35; A61B 90/37; A61B 2034/2055; A61B 34/71;
(Continued)

(56) References Cited

U.S. PATENT DOCUMENTS 4,184,749 A 1/1980 Grossman
5,649,021 A 7/1997 Matey et al.
(Continued)

FOREIGN PATENT DOCUMENTS

JP 07328016 12/1995
JP 11174214 7/1999
(Continued)

OTHER PUBLICATIONS

Indian Office Action dated Feb. 24, 2022 issued in corresponding IN Appln. No. 201917047198.
(Continued)

*Primary Examiner* — Aaron F Roane
(74) *Attorney, Agent, or Firm* — Carter, DeLuca & Farrell LLP (57) ABSTRACT Methods, systems, and computer-readable medium tracks locations of one or more surgical instruments. The method includes detecting a plurality of markers disposed on a distal end of a first surgical instrument within a field of view of a camera, calculating a position of the first surgical instrument based on a location of the plurality of markers within the field of view of the camera, determining the position of the first surgical instrument in relation to a second surgical instrument.

20 Claims, 8 Drawing Sheets (51) Int. Cl.
*A61B 90/00* (2016.01)
*G16H 20/40* (2018.01)
*G16H 30/40* (2018.01)
*G16H 40/63* (2018.01)
*A61B 17/00* (2006.01)
*A61B 34/00* (2016.01)
*A61B 90/50* (2016.01)

(52) U.S. Cl.
CPC ............ *G16H 30/40* (2018.01); *G16H 40/63* (2018.01); *A61B 2017/00216* (2013.01); *A61B 2017/00973* (2013.01); *A61B 2034/2055* (2016.02); *A61B 34/71* (2016.02); *A61B 2034/742* (2016.02); *A61B 2034/743* (2016.02); *A61B 2034/744* (2016.02); *A61B 2090/0807* (2016.02); *A61B 2090/3618* (2016.02); *A61B 2090/3937* (2016.02); *A61B 2090/502* (2016.02)

(58) Field of Classification Search
CPC ........ A61B 2034/742; A61B 2034/743; A61B 2034/744; A61B 2090/0807; A61B 2090/3618; A61B 2090/3937; A61B 2090/502; A61B 2017/00216; A61B 2017/00973; G16H 20/40; G16H 30/40; G16H 40/63
USPC .............................................. 606/1
See application file for complete search history.

(56) References Cited

U.S. PATENT DOCUMENTS

| | | | |
|---|---|---|---|
| 6,324,011 | B1 | 11/2001 | Higuchi |
| 6,927,694 | B1 | 8/2005 | Smith et al. |
| 8,488,243 | B2 | 7/2013 | McKnight et al. |
| 8,830,329 | B2 | 9/2014 | Mao et al. |
| 10,413,373 | B2 * | 9/2019 | Yates ..................... A61B 34/30 |
| 2006/0149418 | A1 | 7/2006 | Anvari |
| 2009/0088634 | A1 | 4/2009 | Zhao et al. |
| 2010/0296723 | A1 * | 11/2010 | Greer ..................... A61B 34/20 |
| | | | 382/153 |
| 2012/0116365 | A1 | 5/2012 | Price et al. |
| 2013/0030571 | A1 | 1/2013 | Ruiz Morales et al. |
| 2013/0128011 | A1 | 5/2013 | Tu et al. |
| 2013/0144307 | A1 | 6/2013 | Jeong et al. |
| 2013/0345718 | A1 * | 12/2013 | Crawford ........... A61B 17/7082 |
| | | | 606/130 |
| 2014/0121834 | A1 | 5/2014 | Ogawa et al. |
| 2015/0005622 | A1 | 1/2015 | Zhao et al. |
| 2015/0049952 | A1 | 2/2015 | Cholayil et al. |
| 2016/0256225 | A1 | 9/2016 | Crawford et al. |

FOREIGN PATENT DOCUMENTS

| | | | |
|---|---|---|---|
| JP | 2008529707 | A | 8/2008 |
| JP | 2009542362 | A | 12/2009 |
| JP | 2010200894 | A | 9/2010 |
| JP | 2011125687 | A | 6/2011 |
| JP | 2013022651 | A | 2/2013 |
| KR | 20120122643 | A | 11/2012 |
| KR | 1020120122643 | | 11/2012 |
| WO | 2008002830 | A2 | 1/2008 |
| WO | 2009/023801 | A1 | 2/2009 |
| WO | 2013012018 | A1 | 1/2013 |

OTHER PUBLICATIONS

Indian Office Action dated Mar. 28, 2022 issued in corresponding IN Appln. No. 201917047199.
Chinese Office Action dated Aug. 22, 2022 issued in corresponding CN Appln. No. 201880033983.5.
Japanese Office Action dated Jul. 29, 2022 issued in corresponding JP Appln. No. 201880006826.5.
Japanese Notice of Allowance dated Aug. 18, 2022 issued in corresponding JP Appln. No. 2019-564993. (Summary only).
Extended European Search Report dated Mar. 4, 2021 corresponding to counterpart Patent Application EP 18806900.9.
International Search Report dated Sep. 3, 2018 and Written Opinion completed Aug. 30, 2018 corresponding to counterpart Int'l Patent Application PCT/US2018/031327.
Japanese Office Action dated Jan. 11, 2022 corresponding to counterpart Patent Application JP 2019-564993.
Japanese Office Action dated Jan. 31, 2022 corresponding to counterpart Patent Application JP 2019-564889.
Japanese Office Action dated Sep. 6, 2022 issued in corresponding JP Appln. No. 2019-564889.
Tobii, e-book, tech.tobii.com. Copyright 2021, Tobii AB, "5 Ways Next-Generation Surgical Robotics Will Leverage Attention to Enhance Care", pp. 1/12-12/12.
Tobii, Tobii White Paper, tech.tobii.com., May 2020, Version 1.0, "Why Next-Generation Surgical Systems Will Include Eye Tracking", pp. 1/15-15/15.

* cited by examiner

SYSTEMS AND METHODS FOR DETECTION OF OBJECTS WITHIN A FIELD OF VIEW OF AN IMAGE CAPTURE DEVICE

CROSS-REFERENCE TO RELATED APPLICATIONS

This application is a National Stage Application of PCT/US2018/031327, filed May 7, 2018 under 35 USC § 371 (a), which claims benefit of and priority to U.S. Provisional Patent Application Ser. No. 62/511,022 filed May 25, 2017, the disclosures of each of the above-identified applications are hereby incorporated by reference in their entirety.

BACKGROUND

Robotic surgical systems are increasingly being used in minimally invasive medical procedures. Typically, robotic surgical systems include a surgeon console located remote from one or more robotic arms to which surgical instruments and/or cameras are coupled. The surgeon console may be located on another side of the operating room from the robotic arms, in another room, or in another building, and includes input handles or other input devices for receiving inputs from a surgeon. The inputs are communicated to a central controller, which translates the inputs into commands for manipulating the robotic arms in the vicinity of the patient.

To view a surgical site, the surgeon console may include a stereoscopic display, sometimes referred to as a three-dimensional (3D) display. In some configurations, in conjunction with a corresponding pair of stereoscopic eyeglasses worn by the surgeon, such displays facilitate depth perception in an image by presenting the image to the surgeon as a pair of distinct images separately provided to the left and right eyes, respectively, replicating the effect of the offset between the left and right eyes, which results in a difference in what is seen in the display by each eye. The different images seen in the display by each eye are perceived as differences in the depths of the objects in the images. In other configurations, the stereoscopic display is viewed without the need for eyeglasses.

The stereoscopic display provides images that are provided from the surgical site via the robotic surgical system. In some configurations of the robotic surgical system, each robotic arm, including those to which one or more cameras as attached, extends from its own base or cart. During preparation prior to surgery, each robotic arm may be moved to various positions in the operating room, depending on the surgeon's preference. To secure each cart in place, each wheel includes a lock or other securing mechanism to prevent movement. During an operation, a camera provides a view of the surgical site. As the surgeon provides inputs to move the robotic arms, and hence, a surgical instrument thereon, the surgical instrument may be moved into and out of the field of view of the camera.

Although the above-described robotic surgical system configuration is adequate, it may be improved. For example, as some medical procedures may be relatively lengthy in duration, maintaining restricted positioning within the console may cause discomfort for some surgeons. Additionally, with regard to the robotic arms, the surgeon may rely on his/her memory to determine the location of one robotic arm and/or instrument relative to another, when the robotic arm and/or instrument has moved out of the field of view of the camera. However, the out-of-view robotic arm may be moved at some point during the procedure, and hence, may not be located where the surgeon last remembered. As a result, the surgeon may need to spend time finding the out-of-view robotic arm, which reduces efficiencies.

SUMMARY

Robotic surgical systems in accordance with the present disclosure allow the surgeon to have improved control over what actions are taken at the patient's bedside and how the actions are implemented.

According to an aspect of the present disclosure, a method is provided for tracking positions of one or more surgical instruments. The method includes detecting a plurality of markers disposed on a distal end of a first surgical instrument within a field of view of a camera, calculating a position of the first surgical instrument based on a location of the plurality of markers detected within the field of view of the camera, and determining the position of the first surgical instrument in relation to a second surgical instrument.

In another aspect of the present disclosure, the first surgical instrument is coupled to a robotic arm and has predetermined points used to calculate the position of the first surgical instrument.

In still another aspect of the present disclosure, calculating the position of the first surgical instrument includes calculating a position of the predetermined points of the robotic arm to identify a position of a base of the robotic arm.

In another aspect of the present disclosure, the method further includes tracking the position of the first surgical instrument by continuously updating the location of the detected plurality of markers.

In still another aspect of the present disclosure, calculating the position of the first surgical instrument includes triangulating a three-dimensional position of the first surgical instrument based upon the location of the detected plurality of markers.

In still another aspect of the present disclosure, the method further includes storing the position of the first surgical instrument.

In another aspect of the present disclosure, the method further includes displaying an indicator on a display identifying the position of the first surgical instrument when the first surgical instrument is outside of the field of view of the camera.

In yet another aspect of the present disclosure, the method includes increasing the field of view of the camera to include the plurality of markers therein.

In another aspect of the present disclosure, the method also includes displaying a warning that the first surgical instrument is no longer within the field of view of the camera.

In still another aspect of the present disclosure, displaying a warning includes prompting the user with a message.

In still another aspect of the present disclosure, the method also includes determining an optimal position for the first surgical instrument within an operating room.

In another aspect of the present disclosure, the method further includes generating a map of the location of the first surgical instrument within the operating room.

In still another aspect of the present disclosure, generating the map includes generating a map showing the relative positions of an operating table and the first surgical instrument.

In still another aspect of the present disclosure, the method further includes disabling an ability to control the first surgical instrument when the detected plurality of markers falls outside the field of view of the camera.

In another aspect of the present disclosure, the method further includes calculating a distance the first surgical instrument is from the field of view of the camera. In still another aspect of the present disclosure, the method further includes displaying the calculated distance on a display device.

In accordance with another aspect of the present disclosure, a robotic surgical system is provided that is configured to track positions of one or more surgical instruments. The robotic surgical system includes a robotic arm coupled to a first surgical instrument, a camera configured to obtain an image of a surgical site, a display configured to display the image of the surgical site obtained from the camera, an image processor configured to detect a plurality of markers disposed on a distal end of the first surgical instrument within a field of view of the camera, and a controller configured to calculate a position of the first surgical instrument based on a location of the plurality of markers within the field of view and to determine the position of the first surgical instrument in relation to a second surgical instrument.

In another aspect of the present disclosure, the robotic arm has predetermined points and the controller is further configured to calculate the position of the first surgical instrument based, in part, on the predetermined points.

In another aspect of the present disclosure, the controller is further configured to calculate the position of the first surgical instrument by calculating a position of the predetermined points of the robotic arm to identify a position of a base of the robotic arm.

In another aspect of the present disclosure, the controller is further configured to track the position of the first surgical instrument by continuously updating the location of the detected plurality of markers.

In still another aspect of the present disclosure, the controller is further configured to calculate the position of the first surgical instrument by triangulating a three-dimensional position of the first surgical instrument based upon the location of the detected plurality of markers.

In still another aspect of the present disclosure, the system further includes a memory coupled to the controller, and the memory stores the position of the first surgical instrument.

In still another aspect of the present disclosure, the controller is further configured to cause the display to display an indicator identifying the position of the first surgical instrument when the first surgical instrument is outside of the field of view of the camera.

In another aspect of the present disclosure, the controller is further configured to increase the field of view of the camera to include the plurality of markers therein.

In another aspect of the present disclosure, the controller is further configured to cause the display to display a warning that the first surgical instrument is no longer within the field of view of the camera.

In another aspect of the present disclosure, displaying a warning includes prompting the user with a message.

In another aspect of the present disclosure, the controller is further configured to determine an optimal position for the first surgical instrument within an operating room.

In still another aspect of the present disclosure, the controller is further configured to generate a map showing the position of the first surgical instrument within the operating room.

In still another aspect of the present disclosure, generating the map includes generating a map showing the relative positions of an operating table and the first surgical instrument.

In still another aspect of the present disclosure, the controller is further configured to disable an ability to control the first surgical instrument when the detected plurality of markers falls outside the field of view of the camera.

In still another aspect of the present disclosure, the controller is further configured to calculate a distance the first surgical instrument is from the field of view of the camera.

In yet another aspect of the present disclosure, the controller is further configured to cause the display device to display the calculated distance.

According to still another aspect of the present disclosure, a non-transitory computer-readable medium having stored thereon instructions which, when executed by a processor, cause detecting a plurality of markers disposed on a distal end of a first surgical instrument within a field of view of a camera, calculating a position of the first surgical instrument based on a location of the plurality of markers detected within the field of view of the camera, and determining the position of the first surgical instrument in relation to a second surgical instrument.

In another aspect of the present disclosure, further instructions are included which, when executed by a processor, cause, calculating the position of the first surgical instrument by using predetermined points on a robotic arm to which the first surgical instrument is coupled.

In another aspect of the present disclosure, further instructions are included which, when executed by a processor, cause calculating the position of the first surgical instrument includes calculating a position of the predetermined points of the robotic arm to identify a position of a base of the robotic arm.

In another aspect of the present disclosure, further instructions are included which, when executed by a processor, cause tracking the position of the first surgical instrument by continuously updating the location of the detected plurality of markers.

In still another aspect of the present disclosure, calculating the position of the first surgical instrument includes triangulating a three-dimensional position of the first surgical instrument based upon the location of the detected plurality of markers.

In another aspect of the present disclosure, further instructions are included which, when executed by a processor, cause storing the position of the first surgical instrument.

In another aspect of the present disclosure, further instructions are included which, when executed by a processor, cause displaying an indicator on a display identifying the position of the first surgical instrument when the first surgical instrument is outside of the field of view of the camera.

In another aspect of the present disclosure, further instructions are included which, when executed by a processor, cause increasing the field of view of the camera to include the plurality of markers therein.

In another aspect of the present disclosure, further instructions are included which, when executed by a processor, cause displaying a warning that the first surgical instrument is no longer within the field of view of the camera.

In still another aspect of the present disclosure, displaying a warning includes prompting the user with a message.

In another aspect of the present disclosure, further instructions are included which, when executed by a processor, cause determining an optimal position for the first surgical instrument within an operating room.

In another aspect of the present disclosure, further instructions are included which, when executed by a processor, cause generating a map of the position of the first surgical instrument within the operating room.

In still another aspect of the present disclosure, generating the map includes generating a map showing relative positions of an operating table and the first surgical instrument.

In another aspect of the present disclosure, further instructions are included which, when executed by a processor, cause disabling an ability to control the first surgical instrument when the detected plurality of markers falls outside the field of view of the camera.

In another aspect of the present disclosure, further instructions are included which, when executed by a processor, cause calculating a distance the first surgical instrument is from the field of view of the camera.

In another aspect of the present disclosure, further instructions are included which, when executed by a processor, cause displaying the calculated distance on a display device.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION

The present disclosure employs optical elements or markers and cameras or image capture devices to determine a position of an object or a person. As will be described in greater detail below, when the markers are detected by the camera or image capture devices, the locations of the detected markers are used to calculate the position of the object or person. Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is farthest from the patient and the term "distal" refers to the portion of the device or component thereof that is closest to the patient.

Figure 1:
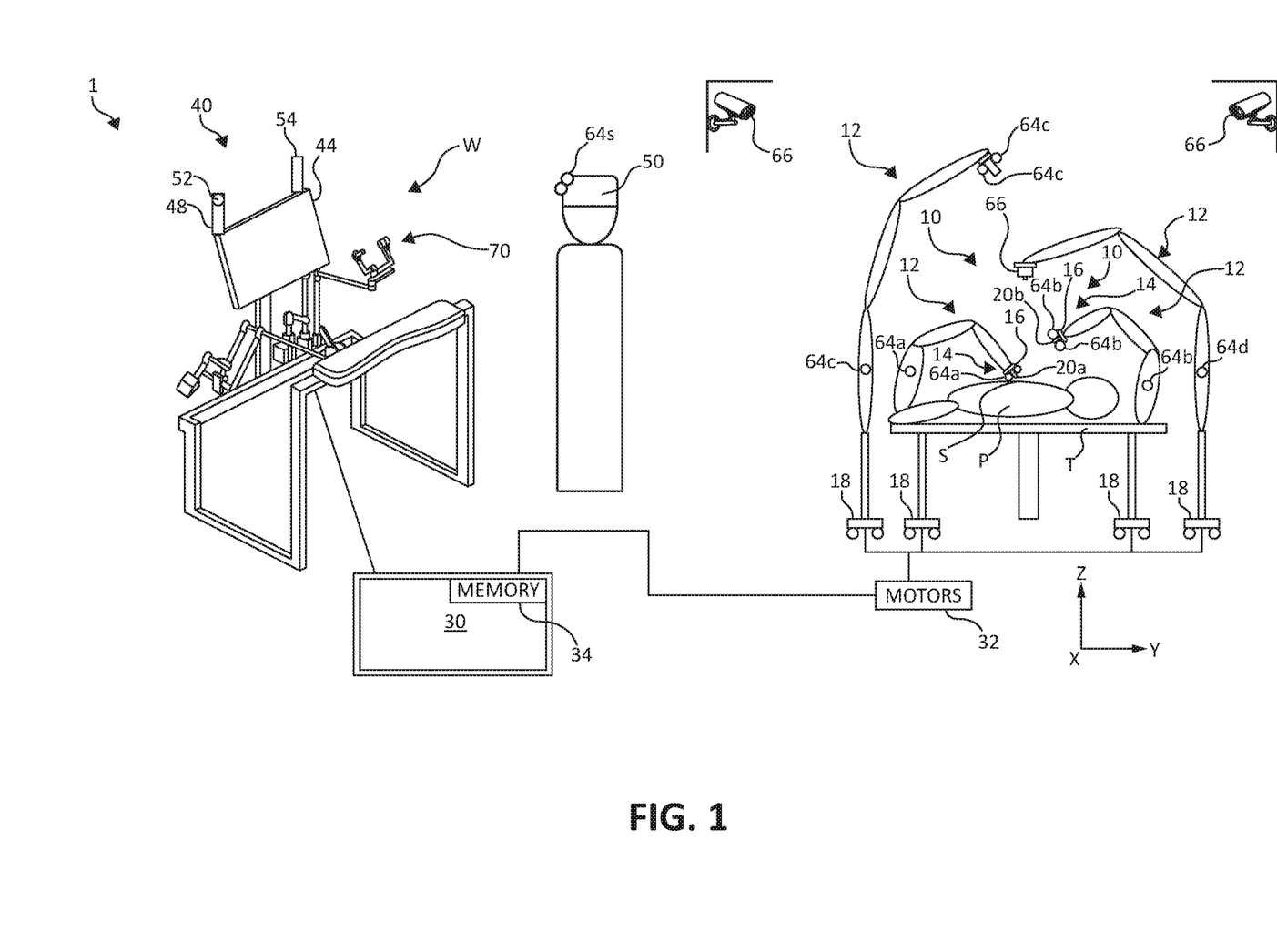
FIG. 1 is a schematic illustration of a robotic surgical system, in accordance with the present disclosure.

With reference to FIG. 1, a robotic surgical system 10 is provided, which is configured for use on a patient "P" lying on an operating table "T" for the performance of a minimally invasive surgical operation. In accordance with an embodiment, the robotic surgical system 10 generally includes a plurality of robotic arms 12 configured to receive commands from a controller 30 for manipulating one or more of the robotic arms 12 in response to an input received at a remotely-located surgeon console 40.

Each of the robotic arms 12 is made up of a plurality of members connected through joints coupled to and extending from a base 18. Each base 18 provides different locations from which each robotic arm 12 extends. For example, the base 18 may be made up of a plurality of movable carts. In another embodiment, all of the robotic arms 12 extend from a single base. In an embodiment, connected to a distal end of each robotic arm 12 is a surgical assembly 14, which includes a surgical instrument holder 16 that is configured to removably couple with a surgical instrument 20. Each robotic arm 12 may include a surgical instrument 20 configured for a different purpose. For example, one robotic arm 12 may include a surgical instrument including a grasping jaw instrument 20, while another robotic arm 12 may include a surgical instrument including scissors. Other suitable instruments 20a, 20b include, but are not limited to, staplers, clip appliers, suture passers, spatulas, and the like.

Although four robotic arms 12 are depicted, the surgical system 10 may include fewer or more than four robotic arms 12. In this regard, the additional robotic arms (not shown) are likewise connected to the controller 30 and are telemanipulatable via the console 40. Accordingly, one or more additional surgical assemblies 14, surgical instrument holders 16, and/or surgical instruments 20a, 20b may also be attached to the additional robotic arms. In another embodiment, one or more of the robotic arms 12 includes an image capture device 66 positioned over the surgical site "S", an image capture device 66 disposed in the surgical site "S" (not shown) or the like. The image capture devices 66 capture visual images, infra-red images, ultrasound images, X-ray images, thermal images, and/or any other known real-time images of the surgical site "S". In an embodiment, the image capture devices 66 include filters, such as band pass filters, for the detection of markers or optical elements 64a-d, 64s (also collectively referred to as markers 64), described in further detail below. In still another embodiment, one or more of the image capture devices 66 are not attached to the robotic arms 12 and are placed at predetermined locations around the operating room. In any case, the image capture devices 66 transmit captured imaging data to the controller 30 which creates images of the surgical site "S" and/or the operating room in real-time from the imaging data and transmits the images to the display device 44 for display. In another embodiment, the displayed images are two-dimensional renderings of the data captured by the image capture devices.

Each of the one or more of the surgical assemblies 14, surgical instrument holders 16, surgical instruments 20a, 20b, and/or the distal end of the robotic arm 12 includes two or more markers 64 that are each attached, coupled, painted, or otherwise placed at predetermined locations on the aforementioned components. The markers 64 are configured to be detectable within a field of view of the image capture devices 66. In an example, the markers 64 may be distinctive painted marks, for example, circles, dots or other filled or unfilled shapes. In another example, the markers 64 may be made of material or include material disposed thereover that is detectable either visibly or in another manner by the image capture devices 66. In particular, the material may be a field of view inhibitor, such as a diffusive and/or reflective element that restricts light reflection to a particular wavelength range, such as the 3M™ Advanced Light Control Film (owned by 3M of Minneapolis, Minnesota) or reflective marker spheres such as those by NDI International of Ontario, Canada. In still another example, the markers 64 may be radio frequency identification tags or other tags capable of emitting waves that are detectable by image capture devices 66 configured to include corresponding detection mechanisms.

The robotic arms 12 may be driven by electric drives (not shown) that are connected to the controller 30. According to an embodiment, the controller 30 is configured to activate drives, for example, via a computer program, such that the robotic arms 12 and the surgical assemblies 14, surgical instrument holders 16, and/or surgical instruments 20a, 20b corresponding to the robotic arms 12, execute a desired movement received through the console 40. The controller 30 may also be configured to regulate movement of the robotic arms 12 and/or of the drives.

The controller 30 may control a plurality of motors 32 with each motor configured to drive a pushing or a pulling of one or more cables, such as cables (not shown) coupled to the surgical instrument 20. In use, as these cables are pushed and/or pulled, the one or more cables effect operation and/or movement of the surgical instruments 20a, 20b. The controller 30 coordinates the activation of the various motors 32 to coordinate a pushing or a pulling motion of one or more cables in order to coordinate an operation and/or movement of one or more surgical instrument 20. In an embodiment, each motor 32 is configured to actuate a drive rod or a lever arm to effect operation and/or movement of surgical instruments 20a, 20b in addition to, or instead of one or more cables.

The controller 30 includes any suitable logic control circuit adapted to perform calculations and/or operate according to a set of instructions. The controller 30 can be configured to communicate with a remote system (not shown) either via a wireless (e.g., Wi-Fi, Bluetooth, LTE, etc.) and/or wired connection. The remote system can include data, instructions and/or information related to the various components, algorithms, and/or operations of console 40. The remote system can include any suitable electronic service, database, platform, cloud, or the like. The controller 30 may include a central processing unit operably connected to memory 34. The memory may include transitory type memory (e.g., RAM) and/or non-transitory type memory (e.g., flash media, disk media, etc.). In some embodiments, the memory is part of, and/or operably coupled to, the remote system.

The controller 30 can include a plurality of inputs and outputs for interfacing with the components of the console 40, such as through a driver circuit. The controller 30 can be configured to receive input signals and/or generate output signals to control one or more of the various components (e.g., one or more motors and/or the display device 44) of the console 40. The output signals can include, and/or can be based upon, algorithmic instructions which may be pre-programmed and/or input by a user. The controller 30 can be configured to accept a plurality of user inputs from a user interface (e.g., switches, buttons, touch screen, etc. of operating the console 40) which may be coupled remote to the system 10.

The memory 34 can be directly and/or indirectly coupled to the controller 30 to store instructions and/or databases including pre-operative data from living being(s) and/or anatomical atlas(es). According to an embodiment, the memory 34 stores data related to the locations of the markers 64a-d, 64s relative to each corresponding instrument, data related to the locations of predetermined points on each of the robotic arms 12, data related to the locations of predetermined points in the operating room (such as locations of corners of the operating room, locations of predetermined points on the floor of the operating room, and the like), data related to locations of predetermined points on the operating table "T", and/or other data useful for the determination of the location of one or more surgical instruments 20a, 20b relative to each other and/or to locations within the operating room. The memory 34 can be part of, and/or or operatively coupled to, the remote system 10.

To provide the input to the controller 30, the surgeon console 40 includes various input devices. In an embodiment, the surgeon console 40 includes input handles 70 or input pedals configured to be manipulated by the surgeon through actuation. In particular, the surgeon uses his or her hands to grip and move the input handles 70 and the movement of the input handles 70 are translated via the controller 30 to thereby provide a corresponding movement to the robotic arms 12 and/or surgical instruments 20a, 20b. The surgeon steps on the input pedals to provide a selection to provide further controls of the robotic arms 12 or the surgical instruments 20a, 20b.

The display device 44 is set up to display two- or three-dimensional images received from the image capture devices 66. In an embodiment in which three-dimensional images are provided, the display device 44 is configured to provide the three-dimensional images for viewing either with or without specialized viewing lenses provided, for example, in the form of a head set 50, such as one configured as glasses or another suitable configuration.

The head set 50 includes markers 64s disposed thereon. In an embodiment, the detection of the markers 64s indicates that the eyes of the surgeon wearing the head set 50 are directed at the display device 44. The markers 64s on the head set 50 may be configured in a similar manner to those included on the surgical assemblies 14, surgical instrument holders 16, surgical instruments 20a, 20b, and/or the distal end of the robotic arm 12. According to an embodiment, the one or more markers 64s are placed at specific locations on the head set 50 such that detection of the markers 64s indicates that the surgeon's head is positioned in a particular manner, for example, looking forward at the display device 44. To detect the markers 64, the surgeon console 40 includes an image capture device 48 mounted to the display device 44 or at another location to allow the image capture device 48 to be directed at the surgeon during system operation. The image capture device 48 may include one or more filters 52, such as a band pass optical filter, for the detection of the markers 64, in an embodiment.

Figure 2:
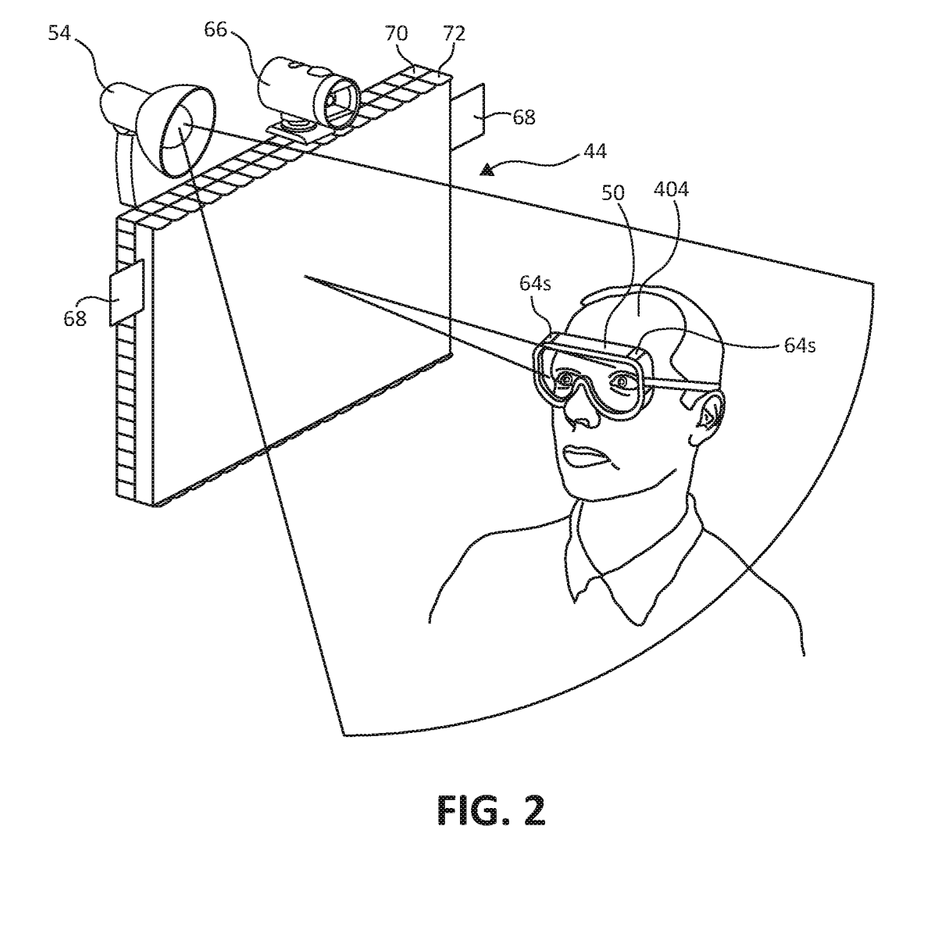
FIG. 2 is a perspective view of a portion of a display system for implementation into the robotic surgical system of FIG. 1, in accordance with the present disclosure.

FIG. 2 is a perspective view of a portion of a display system for implementation into the robotic surgical system 10, showing an example arrangement of the display device 44, the head set 50, a light source 54, the image capture device 48, and audio devices 68, in accordance with various embodiments herein. In an embodiment, the display device 44 includes a screen 70 and one or more layers 72 disposed in front of the screen 70. The screen 70 includes pixels that direct visual content displayed by certain pixels to certain eyes of the surgeon by way of the one or more layers 72. In particular, the one or more layers 72 may include a lenticular lens layer. For example, the lenticular lens layer includes a plurality of vertical lenses disposed over corresponding pixel rows configured to be directed at an angle suitable to permit the visual content of a first set of pixels to be perceived by a first eye of the surgeon and a second set of pixels to be perceived by a second eye of the surgeon.

A light source 54 is configured to provide light and may be mounted along an edge of the display device 44 (as illustrated in FIG. 1) or positioned adjacent, above or below the display device 44. The light source 54 may provide light in the visible and/or invisible spectrum (such as ultraviolet, infrared or the like) to be reflected by markers 64s, which may be included at predetermined locations on the head set 50. The markers 64s may be optical elements including mechanisms to permit the visibility of reflected light when viewed at an angle that is within a predetermined range of angles, in accordance with an embodiment, for detection by the image capture device 48. In an embodiment, the display system is configured such that a notification is provided audibly, for example, by the audio devices 68, tactilely or visually via the display device 44, if the markers 64s are not detected.

Figure 3:
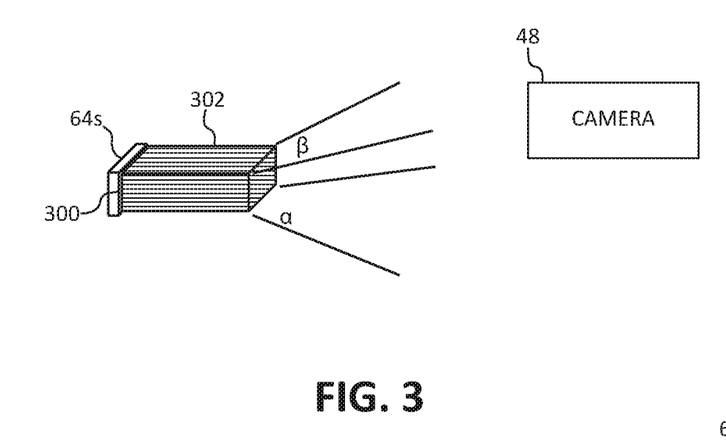
FIG. 3 is a simplified view of a marker and an image capture device for use in robotic surgical system of FIG. 1, in accordance with an embodiment.
Figure 4:
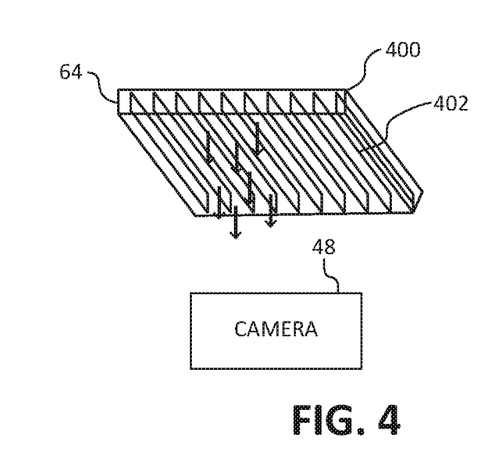
FIG. 4 is a simplified view of a marker and an image capture device for use in robotic surgical system of FIG. 1, in accordance with another embodiment.

As illustrated in FIG. 3, the marker 64s is made up of a reflective element 300 and a diffusive element 302. The reflective element 300 may include a mirror, and the diffusive element 302 may be a tube-shaped element having a rectangular cross-sectional shape, to permit limiting the visibility of the marker 64s by the image capture device 48 by restricting the light reflected by the reflective element 300. Specifically, travel of the reflected light may be restricted horizontally by a first angle R and vertically by a second angle α. Although depicted as having a rectangular cross-sectional shape, the tube-shaped element may have a different cross section shape. In another embodiment, as illustrated in FIG. 4, the marker 64s includes a reflective element 400 and a diffusive element 402, which includes a plurality of tube-shaped elements having rectangular cross-sectional shapes. The tube-shaped elements are substantially identical to each other extending in the same direction and cooperate to limit the light reflected by the reflective element 400 to allow the marker 64s to be detected by the image capture device 48.

Figure 5:
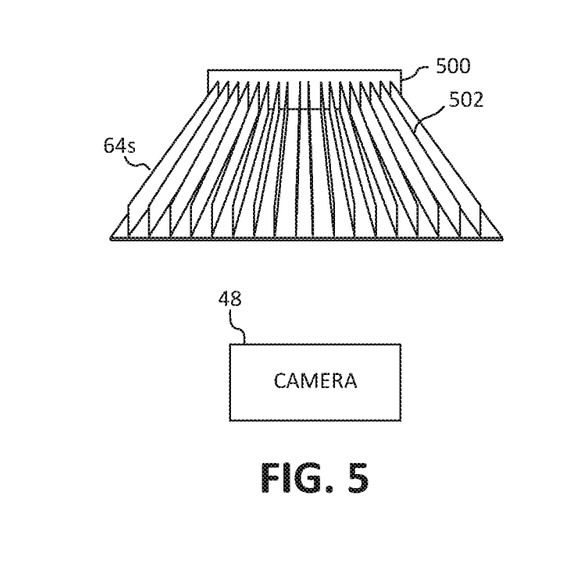
FIG. 5 is a simplified view of a marker and an image capture device for use in robotic surgical system of FIG. 1, in accordance with still another embodiment.

In accordance with another embodiment, the markers 64s may be optical elements including mechanisms to permit the visibility of reflected light when viewed at an angle that is within a predetermined range of angles, for example, as depicted in FIG. 5. Here, the marker 64s has a reflective element 500 and a diffusive element 502, where the diffusive element 502 is in the form of a film with a transparency configured to limit viewing of the marker 64s to the predetermined range of angles. In an embodiment, the diffusive element 502 is configured to allow light directed within a range relative to the reflective element 500 to reflect (for example, a range of viewing angles including an angle substantially perpendicular to the reflective element 500) and to thereby be visible to the image capture device 48. Light directed at the diffusive element 502 at an angle that is outside of the range of viewing angles is not reflected by the reflective element 500 and hence, is not visible to the image capture device 48.

Figure 6:
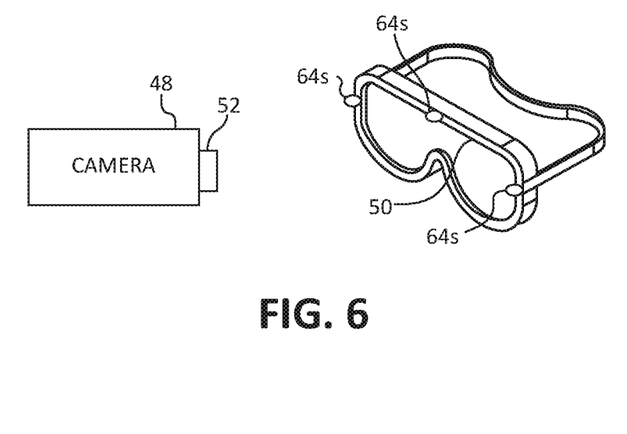
FIG. 6 is a simplified view of a marker on a headset and an image capture device for use in robotic surgical system of FIG. 1, in accordance with an embodiment.

In another embodiment, as depicted in FIG. 6, the markers 64s are configured to reflect light within a particular range of wavelengths (for example, visible or invisible). In such an embodiment, the image capture device 48 includes a bandpass optical filter 52 selected to correspond to the particular range of wavelengths of the markers 64s. Thus, the image capture device 48 detects the markers 64s when the wavelength of light reflected from the markers 64s passes through the bandpass optical filter 52 thereby permitting the image capture device 48 to view the markers 64s. The markers 64s are illustrated as being disposed on a head set 50 in the form of a pair of eyeglasses, in this embodiment. It will be appreciated that the markers 64s alternatively may be included on a headband or other wearable or may be stickers that are placed on various locations of the user's face or head.

Figure 7:
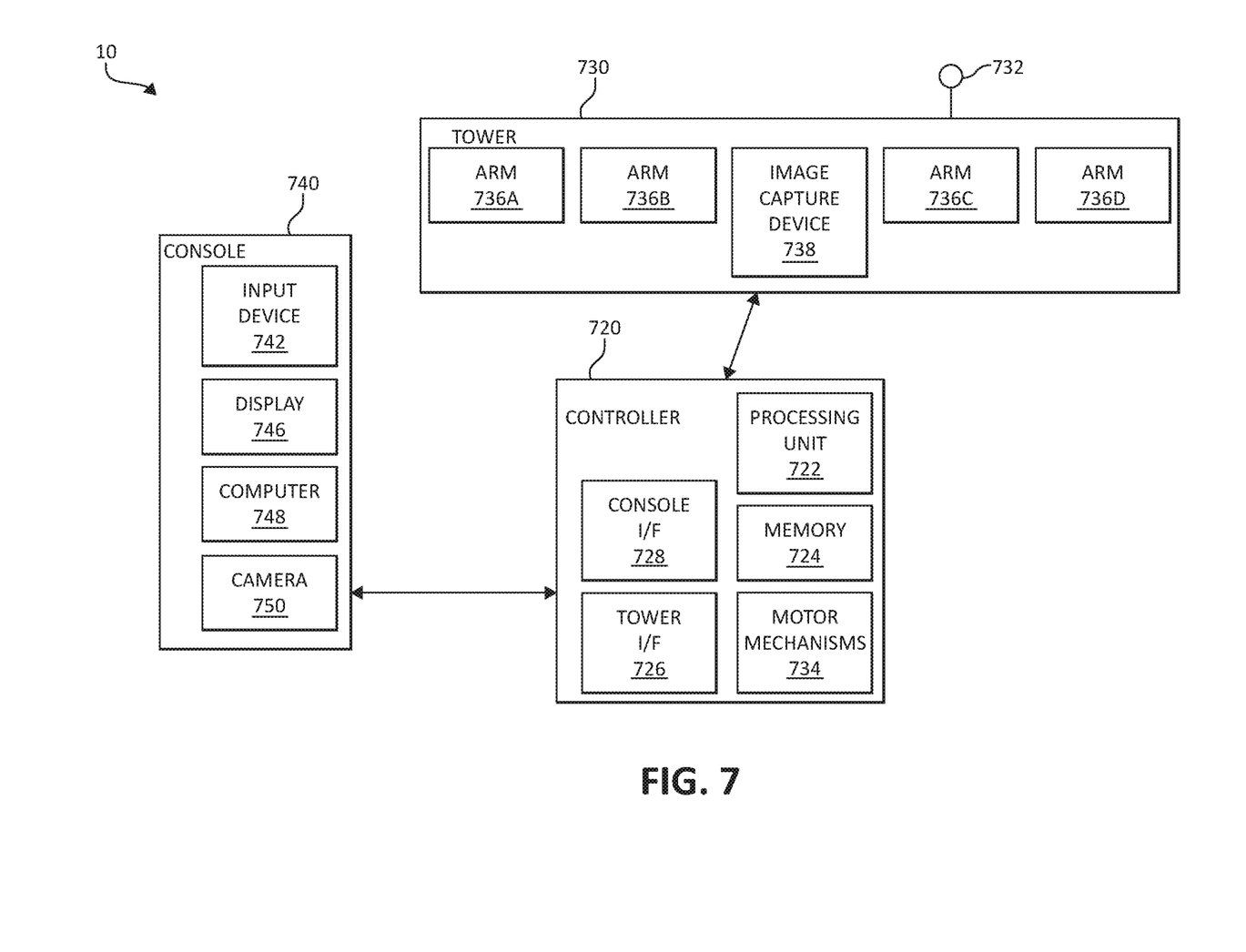
FIG. 7 is functional block diagram of the robotic surgical system, in accordance with the present disclosure.

FIG. 7 is simplified block diagram of the robotic surgical system 10 of FIG. 1. The robotic surgical system 10 includes a controller 720, a tower 730, and a console 740. The controller 720 is configured to communicate with the tower 730 to thereby provide instructions for operation, in response to input received from the console 740.

The controller 720 generally includes a processing unit 722, a memory 724, a tower interface 726, and a console interface 728. The processing unit 722, in particular by means of a computer program stored in the memory 724, functions in such a way to cause components of the tower 730 to execute a desired movement according to a movement defined by input devices 742 of the console 740. In this regard, the processing unit 722 includes any suitable logic control circuit adapted to perform calculations and/or operate according to a set of instructions. The processing unit 722 may include one or more processing devices, such as a microprocessor-type of processing device or other physical device capable of executing instructions stored in the memory 724 and/or processing data. The memory 724 may include transitory type memory (e.g., RAM) and/or non-transitory type memory (e.g., flash media, disk media, etc.). The tower interface 726 and console interface 728 communicate with the tower 730 and console 740, respectively, either wirelessly (e.g., Wi-Fi, Bluetooth, LTE, etc.) and/or via wired configurations. Although depicted as separate modules, the interfaces 732, 734 may be a single component in other embodiments.

The tower 730 includes a communications interface 732 configured to receive communications and/or data from the tower interface 726 for manipulating motor mechanisms 734 to thereby move robotic arms 736a-736d. In accordance with an embodiment, the motor mechanisms 734 are configured to, in response to instructions from the processing unit 722, receive an application of current for mechanical manipulation of cables (not shown) which are attached to the robotic arms 736a-736d to cause a desired movement of a selected one of the robotic arms 736a-736d and/or an instrument coupled to one of the robotic arms 736a-736d. The tower 730 also includes an image capture device 738, which captures real-time images and transmits data representing the images to the controller 730 via the communications interface 732.

To aid the surgeon in manipulating the devices of the tower 730, the console 740 has an input device 742, a display 746, a computer 748, and a camera 750. The input device 742 is coupled to the computer 748 and is used by the clinician to provide an input. In this regard, the input device 742 may be a handle or pedal, or other computer accessory, such as a keyboard, joystick, mouse, button, trackball or other component. The computer 748 includes a processing unit and memory, which includes data, instructions and/or information related to the various components, algorithms, and/or operations of the tower 730 and can operate using any suitable electronic service, database, platform, cloud, or the like. The display 746 receives instructions from the computer 748 to display information received from the image capture device 738 and/or from the communications interface 732. The camera 750 captures images of the surgeon at the console 740.

Figure 8:
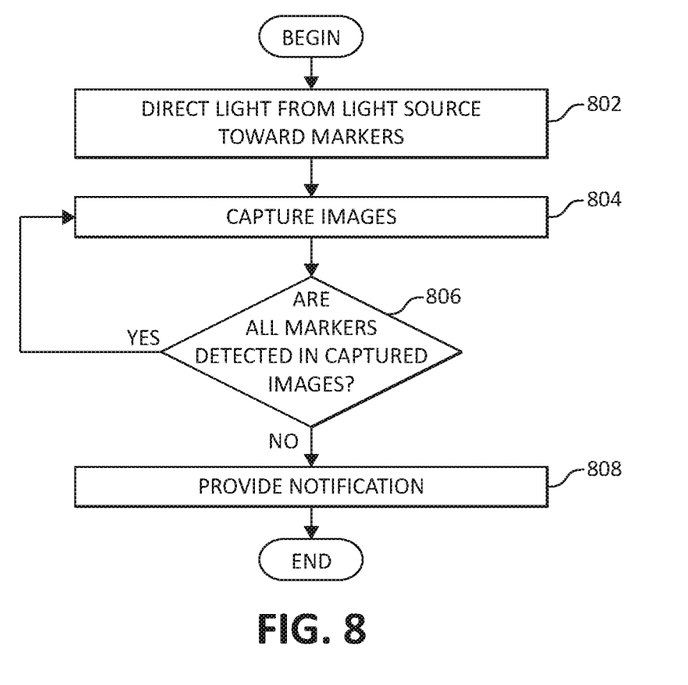
FIG. 8 is a flow diagram of a method for determining positions of a surgeon relative to a display device of the robotic surgical system, in accordance with the present disclosure.

The markers 64 described briefly above are useful for implementing various positioning and safety mechanisms. In an example, during surgery, it may be advantageous for the system 10 to be aware of the positioning of the surgeon relative to the display device 44. Turning now to FIG. 8, a flow diagram of a method 800 is provided for determining the positioning of the surgeon relative to the display device 44 of the robotic surgical system 10, in accordance with an embodiment. The method 800 may be implemented, at least in part, by the processing unit 722 executing instructions stored in the memory 724 (FIG. 7). Additionally, the particular sequence of steps shown in the method 800 of FIG. 8 is provided by way of example and not limitation. The steps of the method 800 may be executed in sequences other than the sequence shown in FIG. 8 without departing from the scope of the present disclosure. Further, some steps shown in the method 800 of FIG. 8 may be concurrently executed instead of sequentially executed.

With reference to FIG. 8, light from the light source 54 is directed toward the markers 64s at step 802. As noted above, the markers 64s are disposed on the surgeon's head or face, for example, on the head set 50. Thus, depending on the positioning of the surgeon's head or face, the markers 64s may or may not reflect the light from the light source 54. For example, in an embodiment, a plurality of the markers 64s are included on the head set 50 at specific locations such that detection of all of the markers 64s indicates that the surgeon's eyes are directed at the display device 44. In another embodiment, the marker or markers 64s at least partially cover the head set 50 to form a specific shape, and detection of the specific shape indicates that the surgeon's eyes are directed at the display device 44.

In any case, to determine whether the one or more markers 64s are detected, the image capture device 48 captures images of the surgeon at step 804. Based on the images from step 804, a determination is made as to whether all of the markers 64s, whether they be a plurality of the markers 64s disposed at the specific locations or one or more markers 64s forming a specific shape, are detected at step 806. If the markers 64s are detected, the method 800 iterates a step 804 to capture additional images of the surgeon using the image capture device 48. If all of the markers 64s are not detected, a notification is provided by the system 10 at step 808 indicating that the surgeon's eyes are not directed at the display device 44. For example, the system 10 may provide an audible notification, via audio devices 68, a tactile notification and/or a visual notification. In accordance with an embodiment, in addition to providing the notification, the system 10 prevents inputs from being received at the input handles 70 or other input devices, such as pedals (if included).

Figure 9:
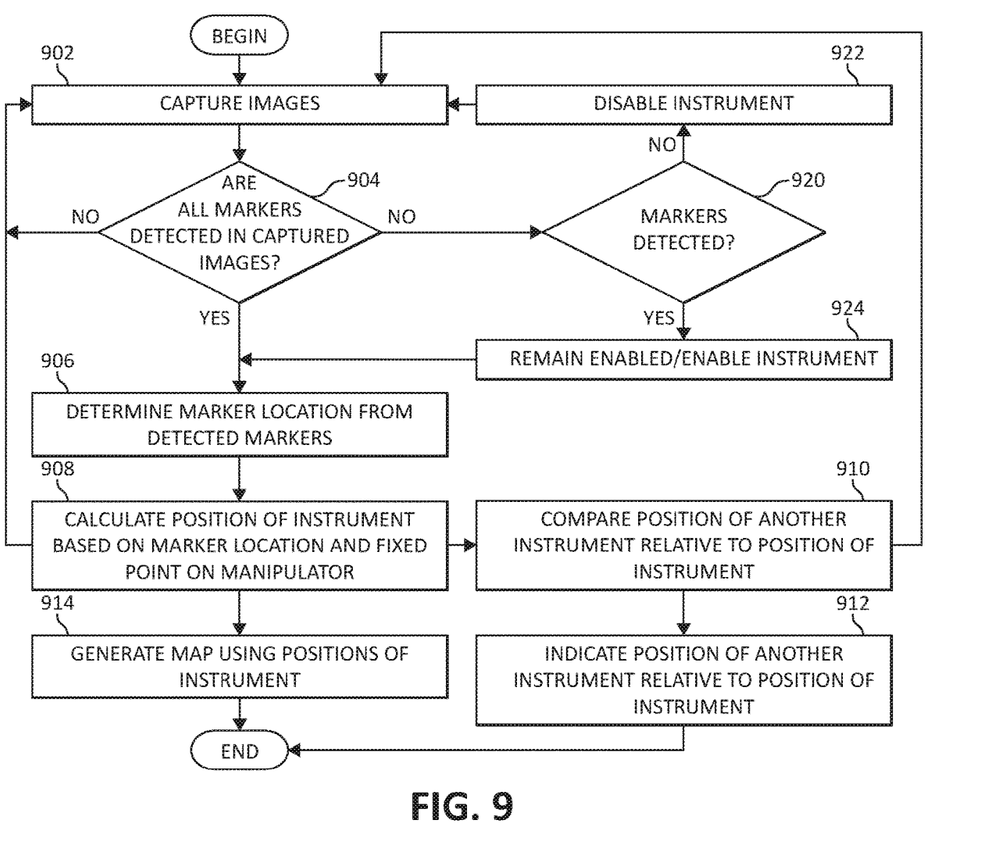
FIG. 9 is a flow diagram of a method for determining positions of components of the robotic surgical system, in accordance with the present disclosure.

In another example, during surgery, it may be advantageous for the clinician to be aware of where each robotic arm 12 and/or surgical instrument 20a, 20b is located. In this regard, the system 10 uses captured image data to detect the location of the markers 64 within the captured image data to thereby determine the position of the robotic arms 12 and/or surgical instruments 20a, 20b. Turning now to FIG. 9, a flow diagram of a method 900 is provided for determining positions of components included in the robotic surgical system 10, in accordance with an embodiment. The method 900 may be implemented, at least in part, by the processing unit 722 executing instructions stored in the memory 724 (FIG. 7). Additionally, the particular sequence of steps shown in the method 900 of FIG. 9 is provided by way of example and not limitation. The steps of the method 900 may be executed in sequences other than the sequence shown in FIG. 9 without departing from the scope of the present disclosure. Further, some steps shown in the method 900 of FIG. 9 may be concurrently executed instead of sequentially executed.

During calibration of the system 10 and/or throughout a surgical procedure, images are captured by the image capture device 66 within a field of view at step 902. In an embodiment in which the image capture device 66 is an endoscope, the images received by the image capture device 66 depict the surgical site "S". The surgical site "S" may be within the patient's body, at an incision site, and/or over the patient's body. In another embodiment, the image capture device 66 is a camera disposed over the patient's body or at a location within the operating room and the images captured by the image capture device 66 are aerial views of the patient or overall views of the operating room. It will be appreciated that the field of view of the image capture device 66 may be limited due to the particular lens configuration of the individual device 66. In any case, the captured images are transmitted to and displayed on the display device 44, which permits the clinician to be aware of the image capture device's 66 field of view.

At step 904, a determination is made as to whether the markers 64a on an instrument 20a are detected within the captured images. The markers 64a on the instrument 20a are included as a set of two or more markers, which are spaced a predetermined distance apart from each other. The placement of each marker in each set is known relative to the other marker(s) in the same set. For purposes of determining the location of the instruments from two-dimensional images, the set of markers includes at least two markers. For purposes of determining the location of the instrument 20a from three-dimensional images, the set of markers 64a includes at least three markers. No matter the particular number of markers in the set of markers, the image is processed, for example, using suitable digital processing algorithms, to detect the presence of the set of markers 64a in the image. The image capture device 66 may be zoomed out to increase the field of view, and the method 300 iterates at step 902 to permit the image capture device 66 to capture additional images.

In another embodiment, to prevent unintended manipulation of an out-of-view instrument 20a, if no markers or only one marker 64 of the set of markers 64a is detected within the field of view of the image capture device 66 at step 904, a determination is made as to whether none of the markers 64a is detected at step 920. If so, the system 10 determines that the instrument 20a is an out-of-view instrument, and the out-of-view instrument 20a becomes disabled at step 922. In particular, an ability to control the out-of-view instrument becomes disabled. The method 900 then iterates at step 902 to capture additional images. If at step 920, any of the markers 64a on the instrument 20a are detected, the corresponding instrument 20a remains enabled or becomes re-enabled at step 924. The instrument 20a becomes re-enabled when the markers are moved back into the field of view of the image capture device 66. In either case, the method 900 proceeds to step 906.

A location of the markers 64a on the instrument 20a is determined from the detected set of markers in the captured images at step 906. According to an embodiment, the locations of the markers 64a are calculated based on the known placement of each of the markers 64a in the set on the instrument 20a. The locations of the markers may be represented by x-y-z coordinates in space, as vectors, or as other suitable spatial location representations.

At step 908, a position of the instrument 20 is calculated based on the location of the markers 64a on the instrument 20a in the captured images and one or more predetermined points on the robotic arm 12 corresponding to the instrument 20a. It will be appreciated that the one or more predetermined points on the robotic arm 12 corresponding to the instrument 20a may be selected from any location on the robotic arm 12, such as a particular location represented by a coordinate in space or the like on one of the corresponding linkages of the robotic arm 12 and/or on the base 18. In an embodiment, the predetermined point on the robotic arm 12 is a marker 64a that has been placed on the robotic arm 12. The predetermined points on the robotic arm 12 corresponding to the instrument 20a and the locations of each of the markers 64a in the set on the instrument 20a are then used to triangulate and calculate the position of the instrument 20a. In particular, in a two-dimensional image, because the two markers 64a on the instrument 20a serve as two points of a triangle while the predetermined point on the robotic arm 12 serves as one point of the triangle, calculations can be made from the three points of the triangle to determine the exact position of the instrument 20a relative to the predetermined point on the corresponding robotic arm 12. In another example, calculations using location(s) of the point(s) of interest of the robotic arm 12 and the instrument 20a to identify the position of a base of the robotic arm 12. One or more of the positions of the instrument 20a and/or the base of the robotic arm 12 at any given time may be stored in the memory 34 for later use. For example, the stored positions of the instrument 20a and/or the base of the robotic arm 12 may be used in determining optimal positioning of the robotic arms 12 for later surgeries.

It will be appreciated that steps 902 to 908 may be reiterated during the course of the operation of the system 10 to track the position of the robotic arm 12 and/or instrument 20a. In an embodiment, the reiteration of steps 902 to 908 allows for continuous updating of the location of the markers 64 and hence, of the arm 12 and/or instrument 20a.

To determine the position of the instrument 20a (also referred to below as "first instrument") relative to the position of another instrument 20b (also referred to below as "second instrument"), the position of the second instrument 20b is compared with the position of the first instrument 20a at step 910. In an embodiment, data including the position of the second instrument 20b is stored in the memory 34 and is compared with the position of the first instrument 20a.

In another embodiment, the position of the second instrument 20b has not yet been determined. In such case, the images captured by the image capture device 66 are used to determine the position of the second instrument 20b. For example, a set of markers 64b on the second instrument 20b is detected from the captured images, such as from the images captured in step 902. For example, both instruments 20a, 20b are captured by the same image capture device 66 and the set of markers 64b on the second instrument 20b is detected from the images used to detect the set of markers 64a on the first instrument 20a at step 904. The method 900 then continues to step 906, where the location of the markers 64b on the second instrument 20b is determined from the detected set of markers 64b in the captured images. Optionally, steps 920 and 922 are performed as well. Next, at step 908, a position of the second instrument 20b is calculated based on the location of the markers 64b on the second instrument 20b in the captured images and one or more predetermined points on the robotic arm 12 corresponding to the second instrument 20b. The calculated position of the second instrument 20b is then compared with the calculated position of the first instrument 20a to thereby determine the location of the first instrument 20a relative to the location of the second instrument 20b.

According to an embodiment, the calculated positions of the first and second instruments 20a, 20b are useful for providing the clinician with improved perspective during the surgical procedure. In this regard, a position of the first instrument 20a relative to the second instrument 20b is indicated at step 912. For example, when the image capture device 66 captures images of the surgical site "S" and only the first instrument 20a is within the field of view of the image capture device 66, an indicator, such as an arrow, may be displayed in the image on the display device 44 to point in a direction in which the second instrument 20b is located relative to the first instrument 20a. In another example, if the two instruments 20a, 20b are being used concurrently, but one instrument, such as the second instrument 20b, is moved out of the field of view of the image capture device 66, the indicator can be displayed pointing in the direction in which the second instrument 20b was moved. In another embodiment, the indicator may be a message instructing the surgeon to increase the field of view of the camera 48. In yet another embodiment, the displayed message includes the distance the second instrument 20b is outside the field of view of the camera. In another embodiment, the indicator is a tactile indication conveyed to the clinician via the input handles 70 or an audible indication conveyed to the clinician via speakers (not shown). In this way, if the clinician wants to begin using the second instrument 20b concurrently with or after usage of the first instrument 20a, the clinician is aware of the position of the second instrument 20b prior to engagement thereof.

In addition to providing orientation to the surgeon, the calculated positions of the first and second instruments 20a, 20b are useful for generating a map showing the positions of the first and second instruments 20a, 20b within the operating room at step 914. In an example, fixed locations within the operating room, such as locations on the floor, on the walls, and/or at the corners of the operating room, are stored within the memory 34 and are used to generate a map of the operating room. The positions of the first and second instruments 20a, 20b, and in some embodiments, the positions of the corresponding bases 18 of the robotic arms 12 to which the instruments 20a, 20b are coupled and/or the location of the operating table "T", if known, are plotted in the generated map of the operating room. The map of the operating room is then displayed to provide the clinician with an overview of the positions of the components of the robotic surgical system, which may be especially useful if the console 40 is located outside of viewing range of the operating room. Moreover, the positions of the instruments 20a, 20b and/or the bases 18 of the robotic arms 12 stored in the memory 34 from previous surgical procedures may be indicated on the generated map and/or may be useful in determining optimal positioning of the robotic arms 12 within the operating room for later surgeries.

Figure 10:
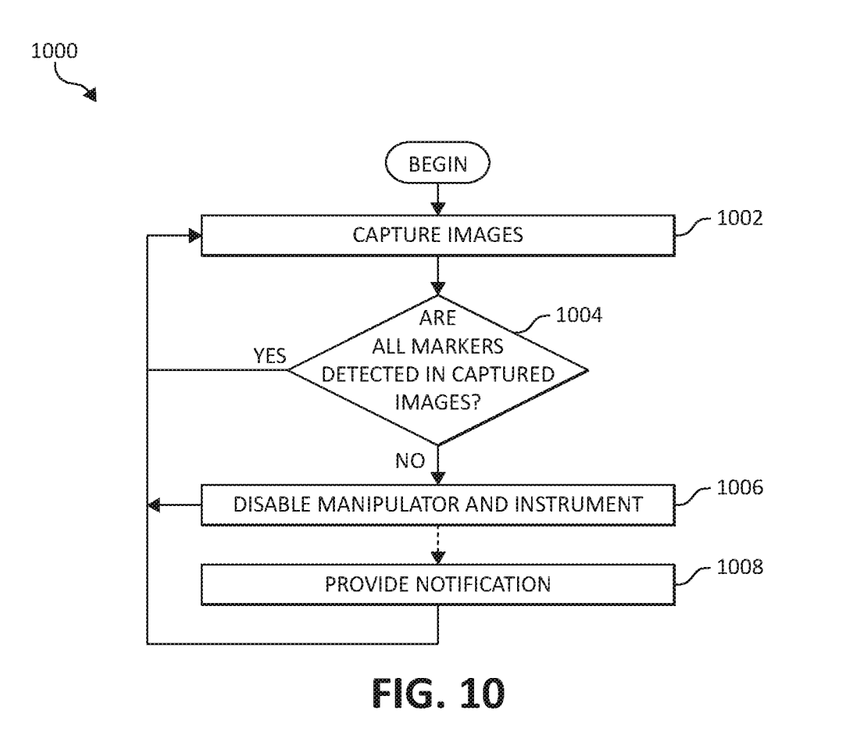
FIG. 10 is a flow diagram of another method for determining the position of a surgeon relative to a display device of the robotic surgical system, in accordance with the present disclosure.

In another example of using the markers 64, in order to provide additional control of the robotic arms 12, the system 10 is configured to further prevent unintended movement by using one or more markers on the head set 50 worn by the surgeon to determine whether the surgeon's eyes are directed at the display device 44. In this regard, the system 10 is configured to capture image data including the head set 50 (on which the one or more markers 64 are disposed) via the camera 48 and to detect the markers 64 within the captured image data. Turning now to FIG. 10 is, a flow diagram of a method 1000 of determining a position of the surgeon's head relative to the display device 44 is provided, in accordance with an embodiment. The method 1000 may be implemented, at least in part, by the processing unit 722 executing instructions stored in the memory 724 (FIG. 7). Additionally, the particular sequence of steps shown in the method 1000 of FIG. 10 is provided by way of example and not limitation. The steps of the method 1000 may be executed in sequences other than the sequence shown in FIG. 10 without departing from the scope of the present disclosure. Further, some steps shown in the method 1000 of FIG. 10 may be concurrently executed instead of sequentially executed.

In an embodiment, images of the surgeon are captured by the camera 48 at step 1002. A determination is then made as to whether one or more of the markers 64 are detected in the captured images, at step 1004. In an embodiment, the camera 48 is configured to detect whether the marker(s) 64 are within its field of view and positioned at a particular angle or location relative thereto. The detection of the markers 64 indicates that the eyes of the surgeon wearing the head set 50 on which the markers 64 are disposed are directed at the display device 44. In an embodiment, the markers 64 include diffusive and/or reflective material, and the camera 48 includes a corresponding filter 52 to allow visual perception of the marker 64 only when the marker 64 is presented at a certain angle. The markers 64 include those types in which the visibility of an optical target is restricted by walls or partitions thereby permitting the optical target to be visually perceived only when viewed at the certain angles. In another example, the markers 64 are constructed from a front surface mirror covered with an engineered transparency film limited to a specific range of angles within which light will be reflected. In another example, the markers 64 include a reflective material covered with an engineered diffuser to limit visibility of the markers 64 to specific angles in horizontal and/or vertical planes, such as those sold by ThorLabs of Newton, New Jersey Thus, when the head set 50 worn by the surgeon is tilted at an angle permitting the light reflected off of the markers 64 and filtered through the filter 52 on the camera 48 to be visible to the camera 48, the markers 64 are then detected. Otherwise, the markers 64 are not detected.

If a determination is made that the marker(s) 64 on the head set 50 are not detected, the system 10 disables movement of the robotic arms 12 and instruments 20a, 20b at step 1006. In an example, inputs received from the input handles 70 are not communicated to the robotic arms 12 or instruments 20a, 20b. In this way, when the surgeon is not looking at the display device 44, the system 10 is prevented from allowing operations which may affect the patient "P." Optionally, a notification is provided at step 408, either on the display device 44, audibly or tactilely to indicate that the surgeon should re-position his or her head to re-enable the functions of the robotic arms 12 and/or instruments 20a, 20b. If a determination is made that the markers 64 are not detected within the field of view of the camera 48, the systems 10 permits operation of the robotic arms 12 and instruments 20a, 20b as usual and iterates at step 1002 to capture additional images.

In accordance with an embodiment, the disabling and enabling of the movement of the robotic arms 12 and/or instruments 20a, 20b depends on whether one of the markers 64 is detected. In another embodiment, the disabling and enabling of the movement of the robotic arms 12 and/or instruments 20a, 20b depends on whether all of the markers 64 included in a set of markers 64 on the head set 50 is detected.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A method of tracking positions of one or more surgical instruments, comprising:
   detecting a plurality of markers disposed on a distal end of a first surgical instrument within a field of view of a camera;
   calculating a position of the first surgical instrument based on a location of the plurality of markers detected within the field of view of the camera;
   determining the position of the first surgical instrument in relation to a second surgical instrument; and
   increasing the field of view of the camera to include the plurality of markers therein when the first surgical instrument is outside of the field of view of the camera.

2. The method according to claim 1, wherein the first surgical instrument is coupled to a robotic arm having predetermined points used to calculate the position of the first surgical instrument.

3. The method according to claim 2, wherein calculating the position of the first surgical instrument includes calculating a position of the predetermined points of the robotic arm to identify a position of a base of the robotic arm.

4. The method according to claim 1, further including tracking the positions of the first surgical instrument by continuously updating the location of the detected plurality of markers.

5. The method according to claim 1, further comprising storing the positions of the first surgical instrument.

6. The method according to claim 1, further comprising displaying an indicator on a display identifying the position of the first surgical instrument when the first surgical instrument is outside of the field of view of the camera.

7. The method according to claim 1, further including displaying a warning that the first surgical instrument is no longer within the field of view of the camera.

8. The method according to claim 7, wherein displaying a warning includes prompting a user with a message.

9. The method according to claim 1, further including calculating a distance the first surgical instrument is from the field of view of the camera.

10. The method according to claim 9, further including displaying the calculated distance on a display device.

11. A method of tracking positions of one or more surgical instruments, comprising:
    detecting a plurality of markers disposed on a distal end of a first surgical instrument within a field of view of a camera;
    calculating a position of the first surgical instrument based on a location of the plurality of markers detected within the field of view of the camera;
    determining the position of the first surgical instrument in relation to a second surgical instrument; and
    determining an optimal position for the first surgical instrument within an operating room.

12. The method according to claim 11, further including generating a map showing the position of the first surgical instrument within the operating room.

13. The method according to claim 12, wherein generating the map includes generating a map showing relative positions of an operating table and the first surgical instrument.

14. The method according to claim 11, further including displaying a warning that the first surgical instrument is no longer within the field of view of the camera.

15. The method according to claim 11, further comprising displaying an indicator on a display identifying the position of the first surgical instrument when the first surgical instrument is outside of the field of view of the camera.

16. The method according to claim 11, further including calculating a distance the first surgical instrument is from the field of view of the camera.

17. A method of tracking positions of one or more surgical instruments, comprising:
    detecting a plurality of markers disposed on a distal end of a first surgical instrument within a field of view of a camera;
    calculating a position of the first surgical instrument based on a location of the plurality of markers detected within the field of view of the camera;
    determining the position of the first surgical instrument in relation to a second surgical instrument; and
    disabling an ability to control the first surgical instrument when the detected plurality of markers falls outside the field of view of the camera.

18. The method according to claim 17, further including displaying a warning that the first surgical instrument is no longer within the field of view of the camera.

19. The method according to claim 17, further comprising displaying an indicator on a display identifying the position of the first surgical instrument when the first surgical instrument is outside of the field of view of the camera.

20. The method according to claim 17, further including calculating a distance the first surgical instrument is from the field of view of the camera.

* * * * *